(12) United States Patent
Takahashi et al.

(10) Patent No.: US 7,488,453 B2
(45) Date of Patent: Feb. 10, 2009

(54) REAGENT VESSEL CAP AND METHOD FOR COLLECTING REAGENT

(75) Inventors: Hiroyuki Takahashi, Tokyo (JP); Eiichiro Tanaka, Tokyo (JP); Hiroyuki Nakamura, Tokyo (JP)

(73) Assignee: Fujirebio Inc., Tokyo (JP)

( * ) Notice: Subject to any disclaimer, the term of this patent is extended or adjusted under 35 U.S.C. 154(b) by 1128 days.

(21) Appl. No.: 10/722,126

(22) Filed: Nov. 26, 2003

(65) Prior Publication Data

US 2004/0170532 A1    Sep. 2, 2004

(30) Foreign Application Priority Data

Nov. 27, 2002    (JP) .............................. 2002-343448

(51) Int. Cl.
*B01L 3/00*    (2006.01)
(52) U.S. Cl. ....................... 422/102; 436/180; 220/260; 220/262
(58) Field of Classification Search ................. 422/102; 220/253, 254.1, 254.5, 254.6, 260, 262, 263; 222/511, 513, 517; 436/180
See application file for complete search history.

(56) References Cited

U.S. PATENT DOCUMENTS

| | | | |
|---|---|---|---|
| 2,378,451 A | | 6/1945 | Vensel |
| 3,384,275 A | | 5/1968 | Simms |
| 4,095,712 A | * | 6/1978 | Perrella ................... 220/254.5 |
| 4,607,768 A | * | 8/1986 | Taber et al. ................. 222/556 |
| 4,776,501 A | * | 10/1988 | Ostrowsky .................. 222/517 |
| 5,273,177 A | * | 12/1993 | Campbell .................... 220/281 |
| 5,735,438 A | * | 4/1998 | Ostrowsky ............. 222/153.06 |
| 5,894,965 A | * | 4/1999 | Robbins et al. ............... 222/444 |
| 5,901,885 A | | 5/1999 | Iida |
| 6,257,452 B1 | | 7/2001 | Allen |
| 6,283,333 B1 | * | 9/2001 | Knickerbocker et al. ...................... 222/153.14 |
| 6,336,574 B1 | * | 1/2002 | Hins .......................... 222/518 |
| 6,763,945 B2 | * | 7/2004 | Baker et al. .................. 206/540 |

FOREIGN PATENT DOCUMENTS

| | | |
|---|---|---|
| DE | AUP.207063 | 1/1960 |
| EP | 0 543 638 A1 | 5/1993 |

(Continued)

OTHER PUBLICATIONS

Japanese Office Action for Corresponding Application No. 2002-343448 Issued Jul. 25, 2006.

*Primary Examiner*—Jill Warden
*Assistant Examiner*—Dwayne K Handy
(74) *Attorney, Agent, or Firm*—McDermott Will & Emery LLP

(57) ABSTRACT

A reagent vessel cap includes a sealing member for sealing the opening of a vessel body; an pressurizing member linked to a retaining part for sealing the sealing member, for bringing the sealing member in close contact with the opening all the time, wherein when pressure is applied, the pressurizing member lifts the sealing member against the biasing force of itself to open the vessel and, when the pressure is eliminated, the pressurizing member returns to position by the biasing force to close the vessel by the sealing member; and a cap body capable of mounting the sealing member and the pressurizing member to the opening of the vessel body containing a reagent. The reagent is collected using the cap structure.

11 Claims, 4 Drawing Sheets

FOREIGN PATENT DOCUMENTS

| | | |
|---|---|---|
| EP | 0 714 834 A1 | 6/1996 |
| JP | 5-294354 | 11/1993 |
| JP | 10-035709 | 10/1998 |
| JP | 11-194132 | 7/1999 |
| JP | 11-304805 | 11/1999 |
| JP | P2000-137032 A | 5/2000 |
| JP | P34-48061 | 7/2003 |
| WO | WO 95/08774 | 3/1995 |

* cited by examiner

REAGENT VESSEL CAP AND METHOD FOR COLLECTING REAGENT

BACKGROUND OF THE INVENTION

1. Field of the Invention

The present invention relates to a cap structure of a vessel used to contain a liquid reagent in analytical instruments which are widely employed for chemistry, biology, and medical treatments and to a method for collecting the reagent without the evaporation of the reagent. More particularly, it relates to a cap attached to the opening of the vessel for sealing it, which is opened only when the reagent is collected, thus allowing the contained reagent to be dispensed and to prevent the evaporation and the like of the reagent and to a method for collecting the reagent by using the cap.

2. Description of the Related Art

Reagents for various analytical instruments used for chemical or biological analysis and determination are generally kept in glass or synthetic resin vessels. In order to prevent the evaporation and contamination of the contained liquid reagents, the openings of the vessels are tightly sealed for supply, transportation, and storage. When they are used, in general, the reagent vessels are stored with the seal cap removed in insulating containers at a specified temperature which are provided to the various analytical instruments and the reagents are automatically collected from the vessels with collecting probes attached to the analytical instruments.

Since the vessels in the insulating container are opened in principle, the liquid reagents stored in the such vessels have many problems to be solved such as the risk of contamination, changes in concentration and composition with passage of time due to the evaporation of moisture and volatile components and the outflow of the reagents due to the tipping of the vessels in handling. Accordingly, various means have been proposed for preventing the contamination, evaporation, and deterioration of the reagents.

For example, Patent Document 1, Japanese Unexamined Patent Application Publication No. 5-294354 (claim 1, FIG. 1) proposes a "cap" which includes a top wall having an opening, a skirt without a screw which is made of a soft material, which is constructed to extend downward from the top wall, and slide on the vessel to come in tight engagement therewith, a slim arm having a sealing device for sealing the opening and moving between a sealing position and an unsealing position, and a biasing device for pushing the arm toward the sealing position.

Patent Document 2, Japanese Unexamined Patent Application Publication No. 11-194132 (claim 1), proposes a cap whose lid is capable of being turned laterally upward from a cap sealing position and having an inclined bistable hinge for opening a vessel and one or more catches capable of coming in contact with a device for pressurizing the cap.

Patent Document 3, Japanese Unexamined Patent Application Publication No. 2000-137032 (claim 1), proposes means for preventing the evaporation of a reagent by holding a liquid having a lower specific gravity than that of the reagent in a vessel, which is not mixed to the reagent, and by covering the surface of the reagent with the liquid.

Furthermore, commercially available analytical instruments use a vessel having an elastic thin sealing member serving as an inside plug at the opening, the sealing member having radial slits from the center, wherein when a reagent-collecting probe is moved downward, it is expanded downward and when the reagent-collecting probe is removed, it returns to a horizontal position by elasticity to cover the opening (Architect i2000, made of Abbott Laboratories).

However, the "cap" which has the mechanically openable and closable section as described in Patent Document 1 has a very complicated structure and so requires a device for pressurizing the "cap" which is set to the vessel when applied to various analytical instruments, thus having problems to be solved in practice such as requiring an additional function and production cost for the vessel.

As described in Patent Document 3, the means for preventing the evaporation of a liquid reagent by covering the surface with a liquid having a lower specific gravity than that of the reagent has not the mechanical structure as in the above-described "cap", offering advantages of no contact between the reagent and air and preventing evaporation. However, since the vessel is always opened, the leakage of the reagent due to tipping of the vessel in handling cannot be prevented.

Furthermore, the commercial inside-plug type necessarily requires slits in a thin seal member serving as an inside plug to form clearance in the plug itself, thus having insufficient effects in preventing evaporation of a reagent and air shield, also requires careful operation in the process of attachment of the plug after the removal of the cap so that the reagent is not contaminated, and particularly has the problem of contamination of a collecting probe and also of the reagent due to contact of the reagent-collecting probe with the sealing member.

SUMMARY OF THE INVENTION

Accordingly, in view of the above-described problems, it is an object of the present invention to provide a reagent vessel cap capable of preventing a change in concentration and deterioration due to evaporation and the like without exposure of a contained liquid reagent to the open air by being attached to the opening of the vessel, allowing repeated collections without the need to be detached from the opening at the collection of necessary amount by the collecting probe of the analytical instrument, and having no possibility of contaminating the collecting probe and the reagent and to provide a method for collecting reagents using the cap structure.

In order to achieve the above object, according to a first aspect of the present invention, a reagent vessel cap is provided which includes a sealing member for sealing the opening of a vessel; a pressurizing member linked to a retaining part for the sealing member to bring the sealing member in close contact with the opening all the time, wherein when pressure is applied, the pressurizing member lifts the sealing member against the biasing force of itself to open the opening and, when the pressure is eliminated, the pressurizing member returns to position by the biasing force to close the vessel by the sealing member; and the sealing member, the retaining part, and the pressurizing member are capable of mounting to the opening of the vessel containing a reagent.

In the reagent vessel cap according to the present invention, preferably, the vessel is self-supported and is shaped like a long and narrow trapezoid in plan view, and has a cylindrical opening having a male screw around the outer periphery at one end of the top and an engaging plate projecting from the other end.

In the reagent vessel cap according to the invention, preferably, the sealing member is formed of a disk-shaped elastic body in general view and integrally has an engaging protrusion in the center of the top, the protrusion having a bulge portion for preventing falling-off at the end.

In the reagent vessel cap according to the invention, preferably, the retaining part is shaped like an inverse cup in general view and integrally has a through hole in the center of the top for receiving the engaging protrusion of the sealing member and integrally has a connecting part extending horizontally at part thereof.

In the reagent vessel cap according to the invention, preferably, the connecting part has a recessed cutout part at the end and integrally has side plates extending downward vertically on the back of the opposite sides of the cutout part, a shaft support on the each side plate at symmetric position and a cylindrical or round-rod-like connecting shaft therebetween.

In the reagent vessel cap according to the invention, preferably, the pressurizing member has an engagement retaining part for engaging and retaining the connecting shaft of the connecting part, at the end of an arm having a slight chevron shape in general view, seen from the side; shaft supports in symmetric positions on the side of the base end thereof; and an elastic arc-shaped arm-supporting member is integrally formed toward the end, on the back near the shaft support.

In the reagent vessel cap according to the invention, preferably, the arm has a hemispherical bulge portion on the surface of a chevron shaped top.

In the reagent vessel cap according to the invention, preferably, the cap body is shaped like a hollow cylinder having a female screw around the inner periphery, the female screw being in engagement with a male screw of the vessel, and integrally has a laterally long housing at part of the outer periphery, the housing having an opening at the top.

In the reagent vessel cap according to the invention, preferably, the housing comprises recessed shaft bearings for receiving shaft supports of the connecting part in opposing side walls near the cap and recessed shaft bearings for receiving the shaft supports of the arm that constitutes the pressurizing member in the side walls apart from the cap body, respectively.

In the reagent vessel cap according to the invention, preferably, the housing integrally includes an undersurface on the inner bottom which always in contact with the end of an arm support member of the pressurizing member, a pair of flexible plates that comes into engagement with a retaining plate formed on the vessel for positioning on the back, and a leg for supporting the housing on the vessel body.

In the reagent vessel cap according to the invention, preferably, the housing is constructed such that the symmetric shaft bearings formed in the side walls apart from the cap are horizontal long holes to allow the arm to be slightly moved to and fro with the rotation of the pressurizing member supported by the shaft bearings.

In the reagent vessel cap according to the invention, preferably, the cap and the housing are molded in one piece of plastic.

According to a second aspect of the present invention, a method for collecting a reagent is provided which includes the steps of: arranging a sealing member attached to a retaining part for a sealing member on the opening of a vessel containing a reagent; tightly sealing the opening with the sealing member by the biasing force of an pressurizing member linked with the retaining part to shield the reagent from outside air; pushing the pressurizing member against the urging force to rotate the linked retaining part upward, thereby opening the vessel; and collecting the reagent.

DESCRIPTION OF THE PREFERRED EMBODIMENT

A preferred embodiment of a reagent vessel cap and a method for collecting reagents according to the present invention will be described hereinafter with reference to the drawings. It is to be understood that various modifications may be made in the invention without departing from the spirit and scope thereof.

Figure 1:
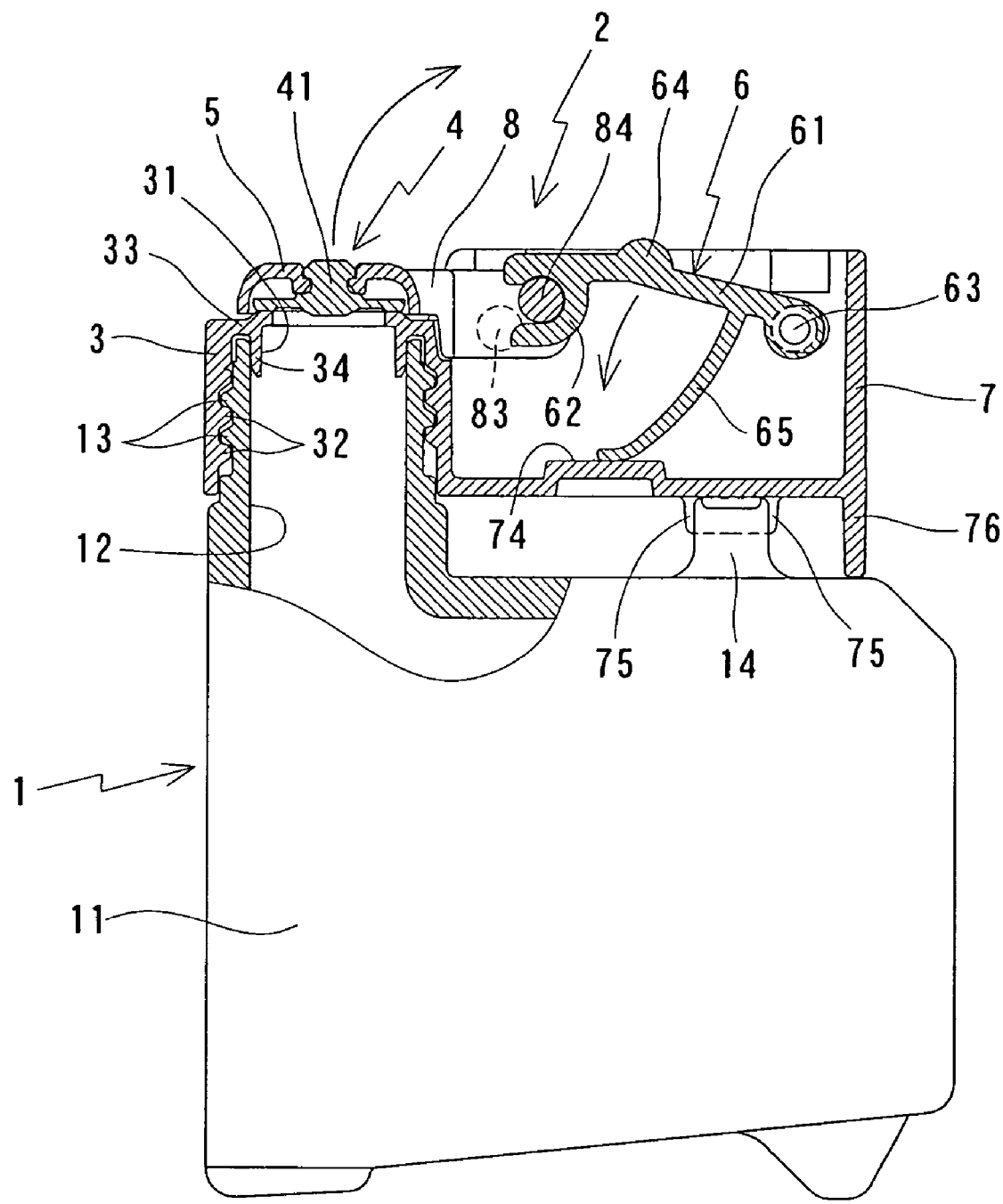
FIG. 1 is a partially cutaway side view of an example of how to use the reagent vessel cap according to the present invention.
Figure 2:
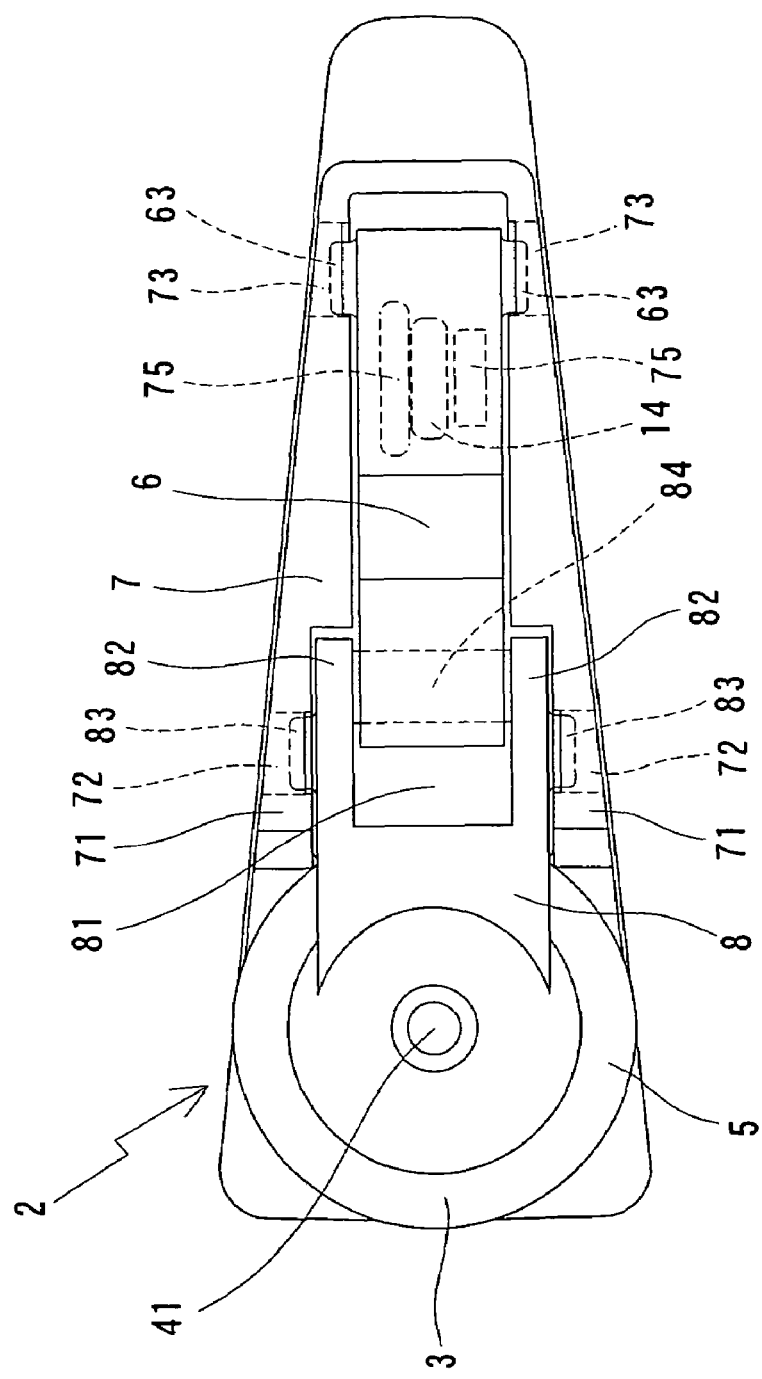
FIG. 2 is a plan view of the cap of FIG. 1.
Figure 3:
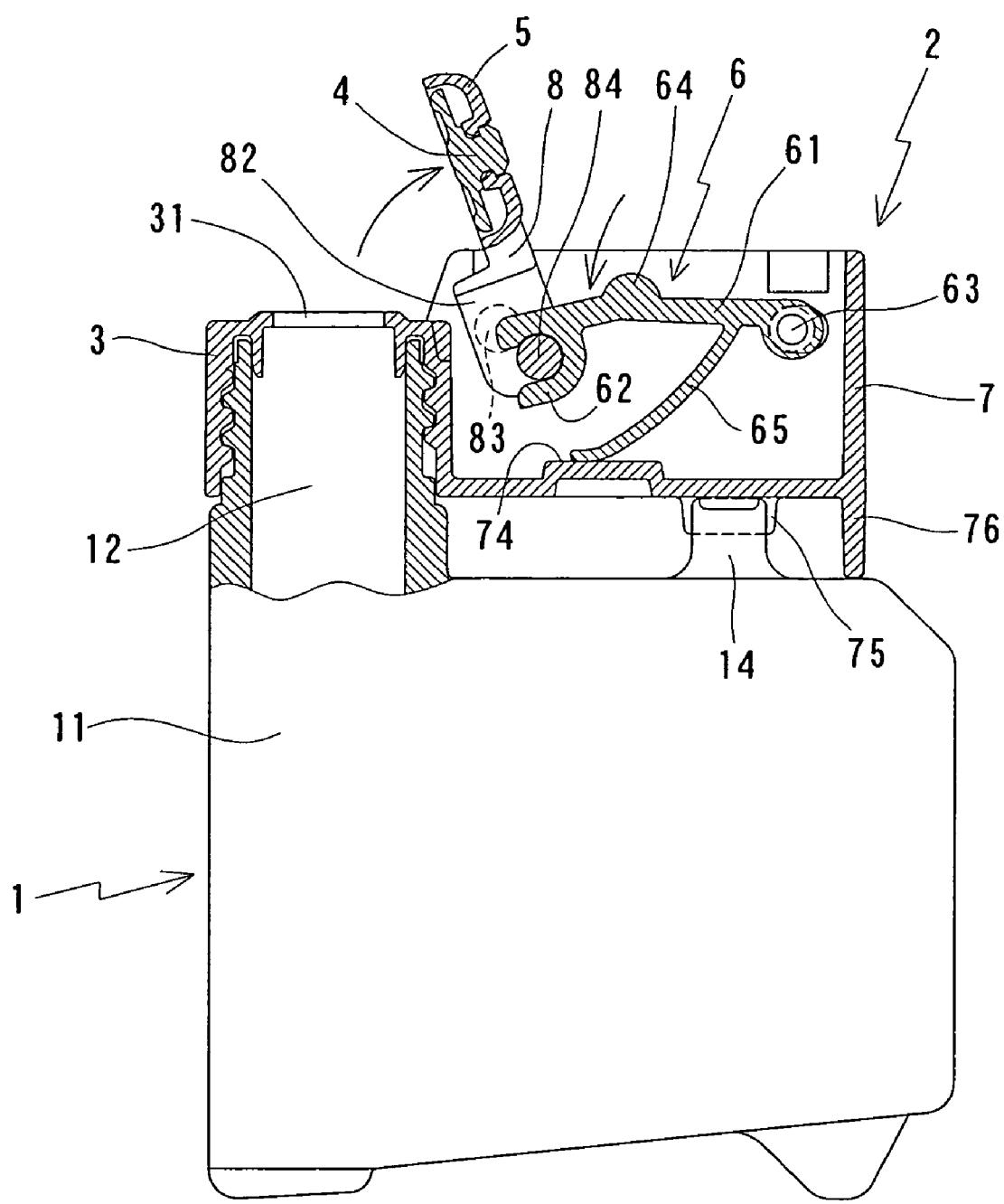
FIG. 3 is a side view of the opening of a reagent vessel in an open state.
Figure 4:
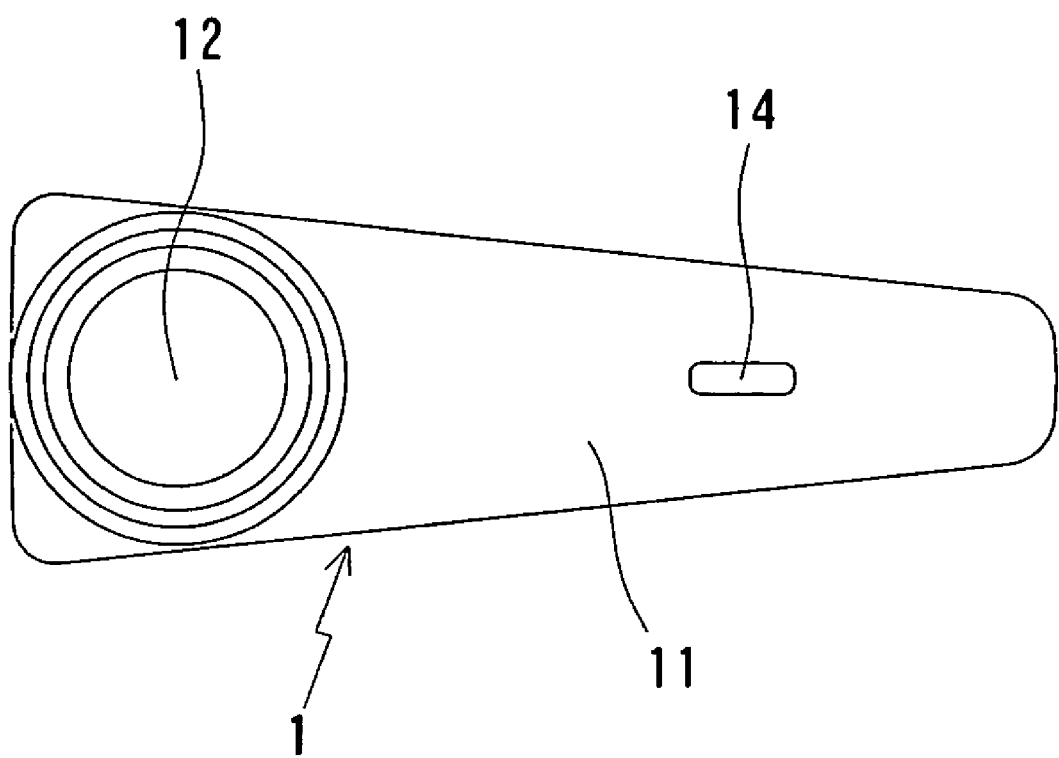
FIG. 4 is a plan view of the reagent vessel.

FIG. 1 is a partially cutaway side view of an example of how to use the reagent vessel cap according to the present invention; FIG. 2 is a plan view of the cap of FIG. 1; FIG. 3 is a side view of the opening of the reagent vessel in an open state; and FIG. 4 is a plan view of the reagent vessel.

In the drawings, numeral 1 denotes a reagent vessel for containing a liquid reagent. A reagent vessel cap 2 (hereinafter, simply referred to as a cap 2) of the invention is attached to an opening 12 of the reagent vessel 1 after a seal cap (not shown) attached to the opening 12 for preventing contamination and evaporation of the contained reagent has been removed when the reagent vessel 1 is hung or stored in an insulating container of an analytical instrument or the like for use in analysis.

The cap 2 is provided as an attachment of the reagent vessel 1 or an analytical instrument. The cap 2 can be attached to individual reagent vessel at the use of the reagent, or alternatively, it can be attached to an analytical instrument in advance and the reagent vessel 1 can be in turn attached to the cap 2.

As clearly shown in FIG. 1, the cap 2 principally includes a cap body 3 attached to the outer periphery of the opening 12 of the reagent vessel 1, a sealing member 4 for tightly sealing an opening 31 of the cap body 3, and an pressurizing member 6 for pushing a retaining part 5 for retaining the sealing member 4 to the opening 31 all the times, and a housing 7 which rotatably holds the pressurizing member 6.

The reagent vessel 1 includes a self-supported vessel body 11 which has a long and narrow trapezoidal shape in plan view and the cylindrical opening 12 projecting from one end of the top of the vessel body 11, having a male screw 13 around the outer periphery of the opening 12 and a locking plate 14 upwardly integrated with the other end of the top. The locking plate 14 may be a picking member attached to conventional reagent vessels.

The cap body 3 is shaped like a hollow cylinder which has substantially the same height as that of the opening 12 and has a female screw 32 around the inner periphery, which is in engagement with the male screw 13 of the opening 12 of the reagent vessel 1, the upper end being bent horizontally along the axis to form a flanged engaging part 33, thus constituting a mount for the sealing member 4.

When the cap body 3 is molded, by forming a ring-shaped extending part 34 extending downward from the back of the engaging part 33, which is in contact with the inside periphery of the opening 12 of the vessel body 11, the cap body 3 can be more securely fitted on the opening 12 of the vessel body 11.

As clearly shown in FIG. 1, the pressurizing member 6 for always pushing the retaining part 5 for fixing the sealing member 4 to the opening 31 and the housing 7 which rotatably holds the pressurizing member 6 are integrated with each other at part of the side of the cap body 3.

The sealing member 4 is made of an elastic body such as natural rubber, synthetic rubber, and thermoplastic elastomer or a soft resin, and is preferably formed of a disk plate having a thickness of about 1 to 2 mm and a diameter to allow contact with the top of the flanged engaging part 33 of the cap body 3, having no particular limit to the thickness, and has an engaging protrusion 41 in the center of the top for retaining it to the retaining part 5 which is drivingly connected to the pressurizing member 6, on the top of which an bulge portion for preventing falling-off is provided.

The retaining part 5 for retaining the sealing member 4 has an opening rim shaped like an inverse cup which is in contact with the top of the cap body 3, having a through hole for the engaging protrusion 41 of the sealing member 4 to pass through in the center of the top and a connecting part 8 integrally formed at the part of the top, which protrudes horizontally toward the housing 7.

Referring to FIG. 2, the connecting part 8 has a cutout part 81 at the end for receiving the end of the pressurizing member 6, on the back of the opposite sides of the cutout part 81, side plates 82 which extend vertically downward are integrally formed, and on the outside of the side plates 82, shaft supports 83 are provided which come in engagement with recessed shaft bearings 72 formed in opposing side walls 71 of the housing 7.

A column- or round-bar-like connecting shaft 84 is placed in position between the side plates 82 and by fitting the shaft supports 83 into the shaft bearings 72 of the housing 7, the connecting part 8 can be rotated upward with the shaft supports 83 as the fulcrum, as shown in FIG. 3.

The pressurizing member 6 has an engagement retaining part 62 at the end of an arm 61 having a slight chevron shape in general view, seen from the side, which has a shape that allows engagement with the connecting shaft 84 and holding the engagement. The pressurizing member 6 also has shaft supports 63 in symmetric positions on the side of the base end thereof. When the shaft supports 63 are fitted in recessed shaft bearings 73 formed in the side walls 71 on the rear of the housing 7, the pressurizing member 6 is rotatably held with the shaft bearings 73 as the fulcrum. Forming the recessed shaft bearings 73 in the side walls 71 of the housing 7 in a horizontal long hole facilitates the operation of the pressurizing member 6.

As clearly shown in FIG. 3, an elastic arc-shaped arm-supporting member 65 is integrally formed on the back near the base end of the arm 61. The end of the arm supporting member 65 is always in contact with an undersurface 74 of the housing 7, which protrudes toward the cap body 3, to hold the arm 61 in the position (a specified position) shown in FIG. 1.

Since the arm 61 has a hemispherical bulge portion 64 at the top of the chevron shape, a pushing part for the pressurizing member 6 can be clearly indicated.

Since the housing 7 is connected to part of the cap body 3, as described above, it is preferably molded of plastic such as polypropylene as an integral part of the cap body 3. In order to fix the attaching position, a pair of flexible plates 75 is provided on the back for holding and positioning the locking plate 14 provided on the upper shoulder of the reagent vessel 1 therebetween when the cap body 3 is screwed on the opening 12 of the reagent vessel 1, and a leg 76 whose end corresponds to the shape of the shoulder surface is provided on the base of the back of the housing 7, which are integrated to one piece.

When the flexible plates 75 are provided on the back of the housing 7, setting the flexible plate 75 located at rotating position longer than the other flexible plate 75 facilitates the engagement with the locking plate 14 to make positioning easy.

In order to mount the cap structure 2 with such a link mechanism to the opening 12 of the reagent vessel 1, after the pressurizing member 6 is rotatably arranged in the housing 7 in advance, the connecting shaft 84 of the connecting part 8 is brought into engagement with the end of the pressurizing member 6, and the whole cap body 3 is then rotated while the female screw 32 of the cap body 3 integrated with the housing 7 is screwed on the male screw 13 of the opening 12 of the vessel body 11, wherein when the female screw 32 and the male screw 13 come in full engagement with each other, the housing 7 is secured to the top of the vessel body 11 and the sealing member 4 fixed to the end of the connecting part 8 tightly seals the opening 31 of the cap body 3 (refer to FIG. 1).

Referring to FIG. 3, when the bulge portion 64 formed on the arm 61 of the pressurizing member 6 is pushed toward the bottom of the housing 7 in this state, the entire pressurizing member 6 is slightly slid toward the opening 31 of the cap body 3 while the arm supporting member 65 is bent by its elasticity and so the end of the arm 61 rotates downward with the shaft supports 63 as the fulcrum.

Therefore, the end of the connecting part 8 that connects to the engagement retaining part 62 at the end of the arm 61 through the connecting shaft 84 is lifted upward with the support shafts 83 as the fulcrum by the downward pressure to the base end, as shown in FIG. 3. Thus, the sealing member 4 integrated with the connecting part 8 is separated from the opening 31 of the cap body 3. When the connecting part 8 is raised substantially into vertical position, a liquid reagent contained in the vessel body 11 can be collected by a necessary amount by bringing down a collecting probe (not shown) vertically from above the opening 31 while holding the state (pressure state).

When the collecting probe is pulled up and the pressure applied to the bulge portion 64 of the arm 61 is relaxed after the collection of the reagent with the collecting probe has been completed, the arm supporting member 65 returns to its initial position by the elastic force of itself and so the arm 61 also returns to its initial position, or a fixed position and, at the same time, the retaining part 5 moves downward toward the opening 31 to seal it and the sealing member 4 tightly seals the opening 31 by the biasing force of the arm supporting member 65, thus preventing the evaporation and contamination of the contained reagent.

In the reagent vessel cap according to the invention, a sealing member arranged on the opening of a vessel body which contains a reagent is linked with an pressurizing member through a retaining part for retaining the sealing member. Accordingly, when the sealing member is brought into close contact with the opening by the biasing force of the pressurizing member, the evaporation and the like of the reagent can be prevented, and when the sealing member is moved upward to open the vessel by applying pressure to the pressurizing member, only a necessary amount of reagent can be collected with a collecting probe in such a state, and thereafter, when the pressure to the pressurizing member is relaxed, the sealing member can be automatically brought into close contact with the opening, thus allowing repeated collections by the collecting probe of an analytical instrument, thus eliminating the need for removing the cap from the vessel at the time of collection, not exposing the contained liquid reagent to outside air, which almost perfectly prevents alterations in regent concentration and deterioration of the reagent due to evaporation and the like.

Particularly, in the reagent vessel cap according to the invention, since the vessel is automatically closed, there is no need to remove the cap from the vessel when the reagent for analytical instruments is placed in an insulating container in the analytical instruments, and there is no possibility that the reagent flows out even when the vessel falls by careless handling. Accordingly, the contained reagent can be collected in various analytical instruments as necessary without consideration of the possibility of contamination and evaporation.

In the reagent vessel cap according to the invention, since the sealing member for tightly sealing the opening of the vessel body is linked with the pressurizing member through the retaining part, the sealing member can be opened and closed in a very short operating distance, making the cap structure more compact and achieving a very simple structure.

By the method for collecting a reagent according to the invention, since the the vessel that contains the reagent is always tightly sealed, the reagent is not exposed to the outside air, thus causing no contamination, alteration in reagent concentration, and deterioration of the reagent due to evaporation and allowing the collecting probe to collect the reagent without contact with the sealing member and the vessel body, eliminating the necessity of removing the cap from the vessel, as in the known art, thus allowing efficient collection.

What is claimed is:

1. A reagent vessel cap comprising:
    sealing member for sealing the opening of a reagent vessel;
    a pressurizing member linked to a retaining part for the sealing member to bring the sealing member in close contact with the opening all the time, wherein when pressure is applied, the pressurizing member lifts the sealing member against the biasing force of itself to open the vessel and, when the pressure is eliminated, the pressurizing member returns to position by the biasing force to close the vessel by the sealing member;
    a long housing attached to the part of an outer periphery of the cap integrally and laterally, and having an opening at a top of the housing, wherein the housing is constructed such that symmetric shaft bearings formed in the side walls of the housing apart from the cap are horizontal long holes to allow an arm of the pressurizing member to be slightly moved to and fro with the rotation of the pressurizing member supported by the shaft bearings;
    wherein the sealing member, the retaining part, and the pressurizing member are capable of mounting to the opening of the vessel containing a reagent.

2. A reagent vessel cap according to claim 1, wherein the sealing member is formed of a disk-shaped elastic body in general view and integrally has an engaging protrusion in the center of the top, the protrusion having a bulge portion for preventing falling-off at an end of the protrusion.

3. A reagent vessel cap according to claim 1, wherein the retaining part has a shape of an inverse cup in general view and integrally has a through hole in the center of a top of the retaining part for receiving the engaging protrusion of the sealing member and integrally has a connecting part extending horizontally at part thereof.

4. A reagent vessel cap according to claim 3, wherein the connecting part has a recessed cutout part at an end of the connecting part and integrally has side plates extending downward vertically on the back of the opposite sides of the cutout part, a shaft support on the each side plate at symmetric positions and a cylindrical or round-rod-like connecting shaft therebetween.

5. A reagent vessel cap according to claim 1, wherein the pressurizing member has an engagement retaining part for engaging and retaining a connecting shaft of a connecting part, at an end of an arm having a chevron shape in general view, seen from the side of the arm; shaft supports in symmetric positions on a side of base end of the arm; and an elastic arc-shaped arm-supporting member is integrally formed toward the end, on the back near the shaft support.

6. A reagent vessel cap according to claim 5, wherein the arm has a hemispherical bulge portion on a surface of a chevron shaped top of the arm.

7. A reagent vessel cap according to claim 1, wherein the cap has a shape of a hollow cylinder having a female screw around the inner periphery, the female screw being in engagement with a male screw of the vessel.

8. A reagent vessel cap according to claim 4, wherein the housing comprises recessed shaft bearings for receiving shaft supports of the connecting part in opposing side walls near the cap and recessed shaft bearings for receiving shaft supports of the arm that constitutes the pressurizing member in the side walls apart from a body of the cap, respectively.

9. A reagent vessel cap according to claim 7, wherein the housing integrally includes an undersurface on an inner bottom of the housing, which is always in contact with an end of an arm support member of the pressurizing member, a pair of flexible plates that comes into engagement with a retaining plate formed on the vessel for positioning on the outer bottom of the housing, and a leg for supporting the housing on the vessel.

10. A reagent vessel cap according to any one of claims 7 to 9, wherein the cap and the housing are molded in one piece of plastic.

11. A method for collecting a reagent, comprising the steps of:
    arranging a sealing member attached to a retaining part for a sealing member on the opening of a vessel containing a reagent;
    setting horizontal long holes of symmetric shaft bearings formed in the side walls apart from a cap to allow an arm to be slightly moved to and fro with a rotation of a pressurizing member supported by the shaft bearings;
    tightly sealing the opening with the sealing member by the biasing force of a pressurizing member linked with the retaining part to shield the reagent from outside air;
    pushing the pressurizing member against the urging force to move slightly the arm and rotate the linked retaining part upward, thereby opening the vessel; and
    collecting the reagent.

* * * * *